United States Patent
Cummins

(10) Patent No.: US 9,820,876 B2
(45) Date of Patent: Nov. 21, 2017

(54) PIVOT OPERATED VASCULAR INTERVENTION DEVICE DELIVERY SYSTEM

(71) Applicant: Cook Medical Technologies LLC, Bloomington, IN (US)

(72) Inventor: Sean Cummins, Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 257 days.

(21) Appl. No.: 14/748,878

(22) Filed: Jun. 24, 2015

(65) Prior Publication Data

US 2016/0074189 A1    Mar. 17, 2016

Related U.S. Application Data

(60) Provisional application No. 62/050,344, filed on Sep. 15, 2014.

(51) Int. Cl.
*A61F 2/06* (2013.01)
*A61F 2/966* (2013.01)
*A61F 2/95* (2013.01)

(52) U.S. Cl.
CPC ...... *A61F 2/966* (2013.01); *A61F 2002/9517* (2013.01)

(58) Field of Classification Search
CPC ............ A61F 2002/0072; A61F 2/2466; A61F 2002/011; A61F 2/95; A61F 2002/9517; A61F 2/954; A61F 2/958; A61F 2002/9583; A61F 2002/9586; A61F 2/962; A61F 2/966; A61F 2002/9665; A61F 2/97

See application file for complete search history.

(56) References Cited

U.S. PATENT DOCUMENTS

| 6,190,360 | B1 | 2/2001 | Iancea et al. | |
|---|---|---|---|---|
| 6,238,402 | B1 | 5/2001 | Sullivan, III et al. | |
| 7,758,625 | B2 * | 7/2010 | Wu | A61F 2/95 623/1.11 |
| 7,967,829 | B2 | 6/2011 | Gunderson et al. | |
| 7,976,574 | B2 | 7/2011 | Papp | |
| 8,062,344 | B2 * | 11/2011 | Dorn | A61F 2/95 606/108 |
| 8,500,789 | B2 | 8/2013 | Wuebbeling et al. | |

(Continued)

*Primary Examiner* — Jonathan Miles
(74) *Attorney, Agent, or Firm* — Liell & McNeil

(57) ABSTRACT

A vascular intervention device delivery system, such as for implanting a self expanding stent, includes a thumbwheel rotatably mounted in a handle. The thumbwheel includes a radially outward thumb surface and a radially outward toothed surface that may be moved into and out of contact with a catch by mounting the thumbwheel on a pivot plate within the handle. The pivot plate may be pivoted with respect to the handle between a locked position to prevent rotation of the thumbwheel, and an unlocked position that permits rotation of the thumbwheel. A catheter has a proximal end attached to the handle, and a distal carrier segment for mounting a vascular intervention device thereon. A retractable sheath is movable from a first position covering the distal carrier segment to a second position retracted proximally uncovering the distal carrier segment. A pull extends between the thumbwheel and the retractable sheath.

19 Claims, 3 Drawing Sheets

(56) References Cited

U.S. PATENT DOCUMENTS

| | | | |
|---|---|---|---|
| 2004/0181239 A1* | 9/2004 | Dorn | A61F 2/95 606/108 |
| 2005/0240254 A1* | 10/2005 | Austin | A61F 2/95 623/1.11 |
| 2005/0273151 A1 | 12/2005 | Fulkerson et al. | |
| 2007/0032860 A1 | 2/2007 | Brooks et al. | |
| 2007/0055342 A1 | 3/2007 | Wu et al. | |
| 2007/0088421 A1 | 4/2007 | Loewen | |
| 2007/0156225 A1 | 7/2007 | George et al. | |
| 2007/0168014 A1 | 7/2007 | Jimenez et al. | |
| 2008/0091257 A1 | 4/2008 | Andreas et al. | |
| 2009/0210046 A1 | 8/2009 | Shumer et al. | |
| 2010/0004606 A1* | 1/2010 | Hansen | A61F 2/95 604/264 |
| 2010/0168756 A1* | 7/2010 | Dorn | A61F 2/95 606/108 |
| 2012/0041537 A1 | 2/2012 | Parker et al. | |
| 2012/0101562 A1 | 4/2012 | Gunderson et al. | |
| 2012/0123516 A1 | 5/2012 | Gerdts et al. | |
| 2012/0158120 A1 | 6/2012 | Hacker et al. | |
| 2012/0330401 A1 | 12/2012 | Sugimoto et al. | |
| 2013/0013047 A1 | 1/2013 | Ramos et al. | |
| 2013/0018451 A1 | 1/2013 | Grabowski et al. | |
| 2013/0110223 A1 | 5/2013 | Munsinger et al. | |
| 2013/0304187 A1* | 11/2013 | Yamashita | A61F 2/966 623/1.12 |

* cited by examiner

PIVOT OPERATED VASCULAR INTERVENTION DEVICE DELIVERY SYSTEM

TECHNICAL FIELD

The present disclosure relates generally to vascular intervention device delivery systems, and more particularly to a feature that holds the thumbwheel against rotation in one direction, but permits rotation in an opposite direction for deployment of a vascular intervention device.

BACKGROUND

Self expanding stents and similar vascular intervention devices are often delivered and deployed using so called pin and pull systems. Typically, the stent is compressed between a retractable outer sheath and an inner catheter. To deploy the stent, the user has to pull the outer sheath to uncover the stent using one hand while resisting the force with the other hand on the inner catheter to maintain the position of the stent during deployment. In pin and pull systems, the user can have difficultly maintaining the inner catheter at a fixed position while simultaneously moving the outer sheath. In very difficult stent deployments, which require a large amount of force by the user, this simultaneous push and pull may lead to inaccurate stent positioning, shortening or lengthening of the stent, or possibly even damage to the stent or target vessel. Another disadvantage of pin and pull systems is that there can be a lack of control on the deployment because the force to deploy the stent decreases as more of the stent is deployed. If the user maintains the same high force during deployment, the stent may be deployed too fast for the user to control. Another potential problem relates to building up tension in the outer sheath prior to movements thereof during the deployment process. If the user pauses during the deployment and releases this built up tension, deployment errors can occur when the user resumes tension to again move the outer sheath to the deployment position fully uncovering the self explaining stent.

The present disclosure is directed toward one or more of the problems set forth above.

SUMMARY OF THE DISCLOSURE

In one aspect, a vascular intervention device delivery system includes a handle with a catch positioned therein. A pivot plate is mounted in the handle, and is pivotable about a first axis with respect to the handle between a locked position and an unlocked position. The pivot plate supports an axle that defines a second axis. A thumbwheel is rotatably mounted on the axle and has a radially outward thumb surface and a radially outward toothed surface. The radially outward toothed surface is in contact with the catch when the pivot plate is at the locked position to prevent rotation of the thumbwheel in a forward direction, and the radially outward toothed surface is out of contact with the catch when the pivot plate is at the unlocked position to permit rotation of the thumbwheel in a reverse direction. A catheter has a proximal end attached to the handle, and has a distal carrier segment for mounting a vascular intervention device thereon. A retractable sheath is movable from a first position covering the distal carrier segment to a second position retracted proximally uncovering the distal carrier segment. A pull extends between the thumbwheel and the retractable sheath. The retractable sheath moves responsive to rotation of the thumbwheel in the reverse direction.

In another aspect, a method of operating the vascular intervention device delivery system includes pivoting the pivot plate from the locked position to the unlocked position. The thumbwheel is rotated in the reverse direction to build up tension in the retractable sheath and pull without moving the retractable sheath relative to the distal carrier segment of the catheter. A portion, which is less than all, of the distal carrier segment is uncovered by continuing to rotate the thumbwheel in the reverse direction. Rotation of the thumbwheel in the reverse direction is paused. The pivot plate is pivoted from the unlocked position to the locked position. Tension in the pull and the retractable sheath is maintained by preventing rotation of the thumbwheel in the forward direction. The pivot plate is again pivoted form the locked position to the unlocked position. A remaining portion of the distal carrier segment is uncovered by resuming rotation of the thumbwheel in the reverse direction.

DETAILED DESCRIPTION

Figure 1:
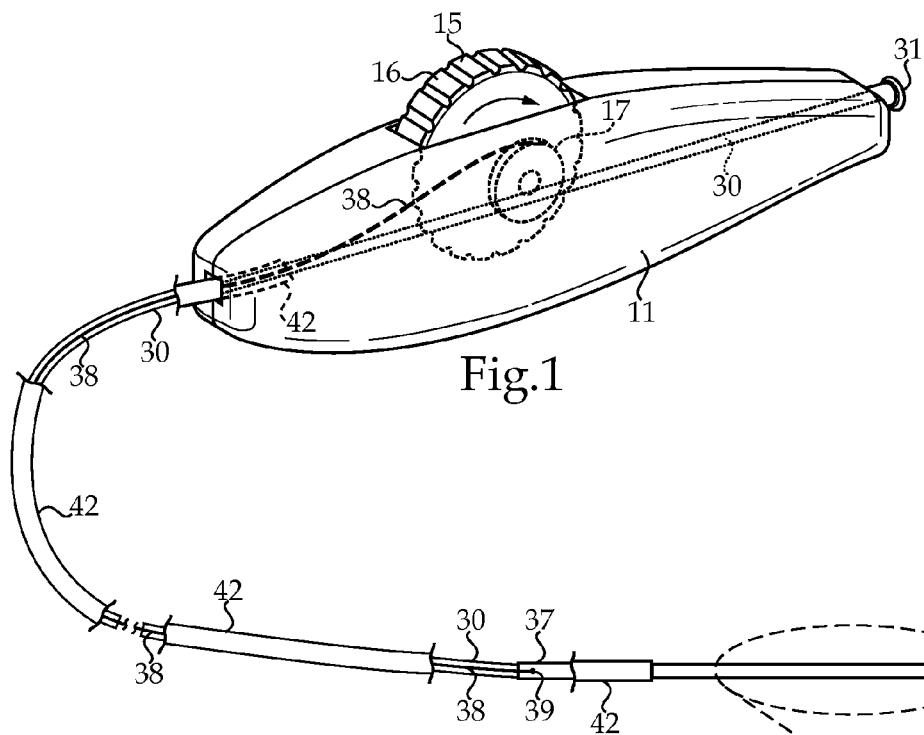
FIG. 1 is a perspective schematic view of a vascular intervention device delivery system according to the present disclosure.
Figure 2:
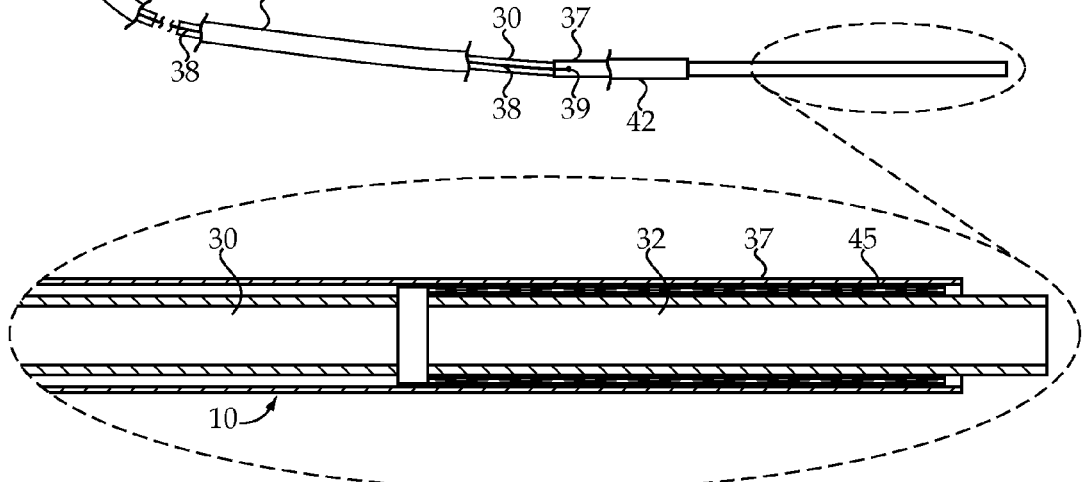
FIG. 2 is an enlarged view of the distal segment of the delivery system shown outlined with a dashed line in FIG. 1.
Figure 3:
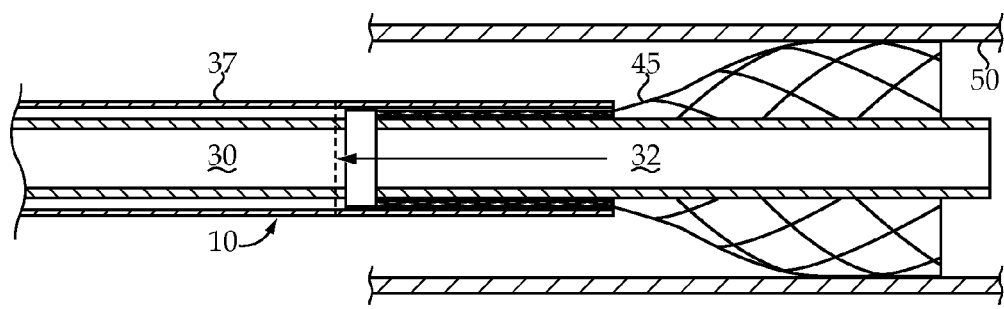
FIG. 3 is a view similar to FIG. 2 about half way through a deployment of a self expanding stent.

Referring to FIGS. 1-3, a vascular intervention device delivery system 10 is shown before and during delivery of a self expanding stent 45 into the vessel 50 of a patient. Delivery system 10 includes a handle 11 that may be gripped in one hand by a user during a delivery procedure. Handle 11 may, for instance, be manufactured from a suitable molded plastic, such as in two longitudinal halves that are joined in any suitable manner to form the complete handle 11. A thumbwheel 15 is rotatably mounted in the handle 11 and has a radially outward thumb surface 16 and a spool 17. A catheter 30 has a proximal end 31 attached to handle 11, and a distal carrier segment 32 for mounting a vascular intervention device, such as a self expanding stent 45, thereon. Proximal end 31 may take the form a Luer lock fitting so that treatment fluids or the like may be injected through catheter 30 in a manner well known in the art. A retractable sheath 37 is movable with respect to catheter 30 from a first position covering the distal carrier segment 32 to a second position indicated by the dashed line in FIG. 3 at which the retractable sheath 37 has been retracted proximally to uncover the distal carrier segment 32. FIG. 3 shows the retractable sheath 37 about half way between the first position and the second position.

A pull 38 extends between the spool 17 of thumbwheel 15 and the retractable sheath 37. Pull 38, which preferably is less elastic than the retractable sheath 37, may be attached to retractable sheath 37 at an attachment 39 in any manner known in the art. In most versions of the vascular intervention device delivery system 10 of the present disclosure, pull 38 will be longer than retractable sheath 37. Nevertheless, retractable sheath 37 could be longer than pull 38 without departing from the present disclosure. Pull 38 may comprise a metallic wire or thin band of metal.

A wire retention/stability sheath 42 surrounds a majority of the length of pull 38, and serves to keep pull 38 in close proximity to the outer surface of catheter 30 over much of the length of delivery system 10. Wire retention/stability sheath 42 may be unattached to catheter 30, pull 38 or retractable sheath 37, but may be attached to move with pull 38 and/or retractable sheath 37. On the other hand, wire retention/stability sheath 42 may be attached to catheter 30 at one or more locations so that pull 38 and retractable sheath 37 also move with respect to wire retention/stability sheath 42 during the delivery process. Wire retention/stability sheath 42 may terminate at its proximal end at a fixation point within handle 11.

When in its pre-deployment configuration, as shown in FIGS. 1 and 2, a vascular intervention device, such as a self expanding stent 45, is disposed between an outer surface of the distal carrier segment 32 of catheter 30, and an inner surface of the retractable sheath 37. During a typical procedure, the distal carrier segment 32 is positioned at a treatment location within a vessel 50 of a patient. After achieving proper positioning, the user then grips handle 11 and begins to rotate thumbwheel 15 so that pull 38 is wound onto spool 17. As this occurs, pull 38 and retractable sheath 37 move proximally with respect to catheter 30 to allow the self expanding stent 45 to expand away from carrier segment 32 and into contact with the inner wall of vessel 50 in a manner well known in the art. During this process, catheter 30 is placed in compression while both pull 38 and retractable sheath 37 are in tension. According to the present disclosure, handle 11 and thumbwheel 15 include a structure that allows thumbwheel 16 to rotate to wind pull 38 onto spool 17, but prevent rotation in an opposite direction. This aspect of the disclosure allows the user to stop the deployment procedure while retaining the stored elastic energy in pull 38 and retractable sheath 37.

Figure 4:
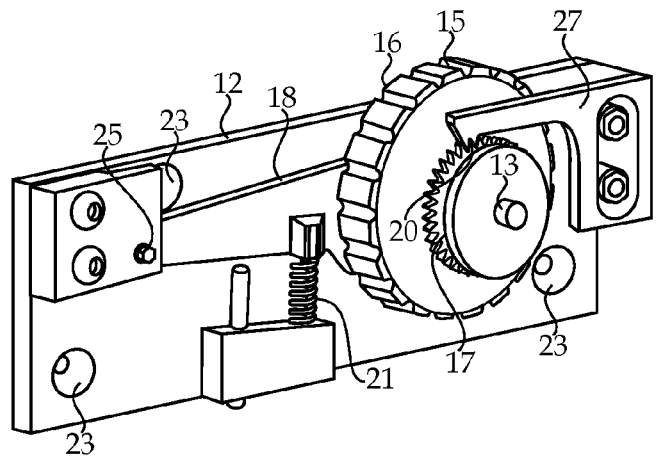
FIG. 4 is a perspective view of an assembly plate for the handle shown in FIG. 1.
Figure 5:
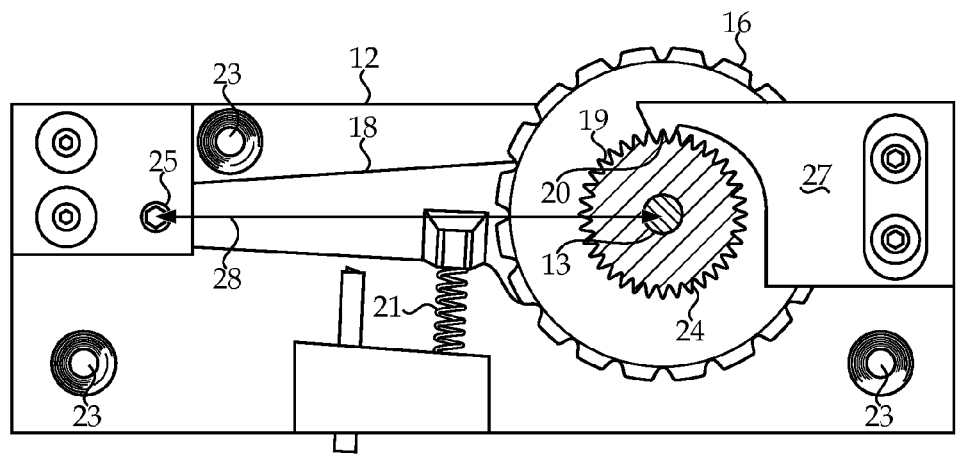
FIG. 5 is a partial sectioned view showing the pivot plate in the locked position according to the present disclosure.
Figure 6:
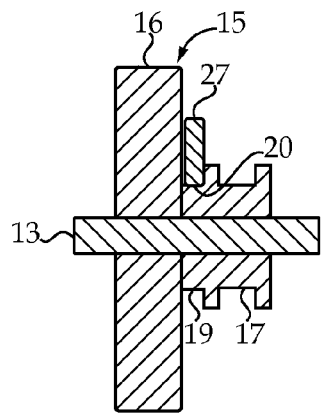
FIG. 6 is a sectioned side view through the thumbwheel of FIGS. 1, 4 and 5.

Referring now in addition to FIGS. 4-6, the interaction between a catch 20 and a radially outward toothed surface 19 of thumbwheel 15 provides the structure by which the thumbwheel 15 can be prevented from rotating after tension has been built up in the pull 38 and retractable sheath 37. In particular, handle 11 may be formed to include, or have attached to an inner surface, an assembly plate 12. Assembly plate 12 may include mounting bores 23 for attachment to an inner surface of handle 11 in a conventional manner, such as by use of fasteners. Catch 20 may be a portion of a catch plate 27 that is mounted to assembly plate 12, such as by the use of two fasteners in a slotted connection. A pivot plate 18 is mounted to assembly plate in handle 11 at an axis 25. Pivot plate 18, is pivotable about axis 25 with respect to handle 11 between a locked position (as shown) and an unlocked position. The pivot plate 18 supports an axle 13 that defines an axis of rotation 14 for thumbwheel 15. Thumbwheel 15 is rotatably mounted on axle 13 and includes both the radially outward thumb surface 16 and a radially outward toothed surface 19. The radially outward toothed surface 19 is in contact with the catch 20 when the pivot plate 18 is at the locked position (as shown) to prevent rotation of the thumbwheel in a forward direction, and the radially outward toothed surface 19 is out of contact with the catch 20 when the pivot plate 18 is at the unlocked position to permit rotation of the thumbwheel in a reverse direction to deploy the self-expanding stent 45. A spring 21 may be operably positioned to bias the pivot plate 18 toward the locked position. Although not necessary, the radially outward toothed surface 19 may include a plurality of teeth 24 in each of four 90° rotation angles. In the embodiment shown, the radially outward toothed surface 19 includes at least thirty teeth 24 around its circumference.

In the illustrated embodiment, pull 38 may comprise a metallic band that is oriented perpendicular to both the thumbwheel axis 14 and the pivot plate axis 25, which are oriented parallel to each other. The pivot axis 25 may be separated from the thumbwheel axis 14 by a distance 28 that is greater than a diameter of thumbwheel 15.

Figure 7:
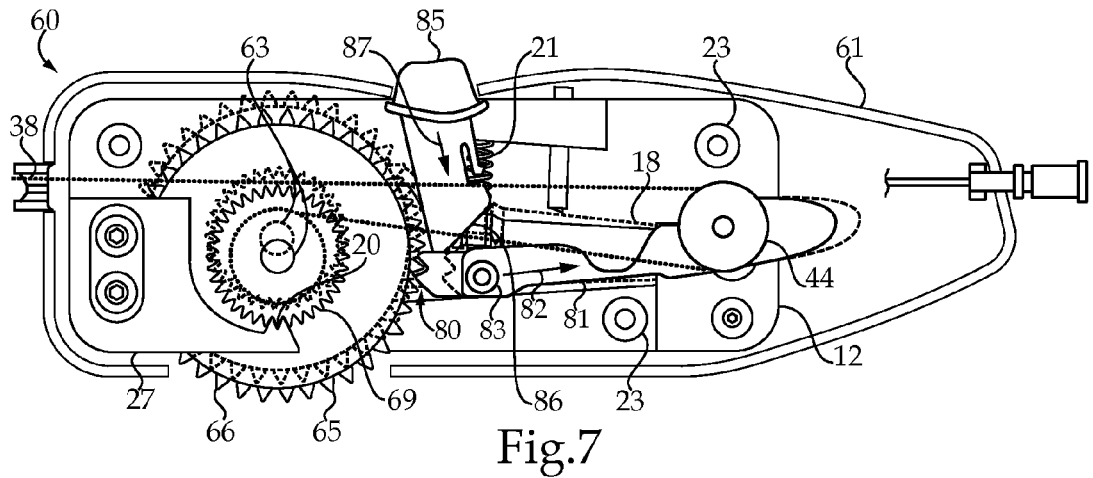
FIG. 7 is a sectioned side view of a handle portion of a vascular intervention device delivery system according to another aspect of the present disclosure.
Figure 8:
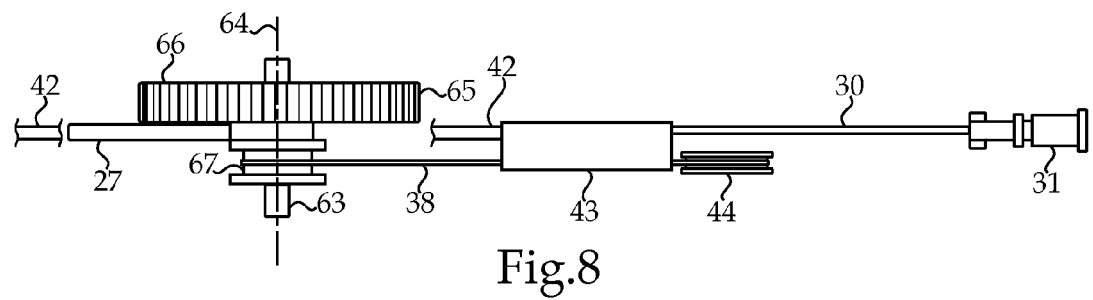
FIG. 8 is a top view of the inner workings of the vascular intervention device delivery system of FIG. 7, minus the handle and the assembly plate.
Figure 9:
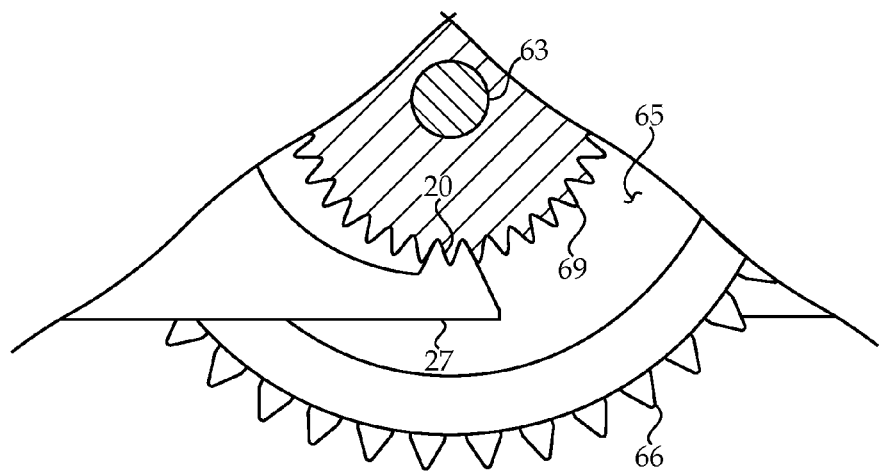
FIG. 9 is an enlarged side view of a catch for the vascular intervention device delivery system of FIG. 7 engaging the radially outward toothed surface of the thumbwheel.

Referring now to FIG. 7-9, a vascular intervention device delivery system 60 according to another aspect is very similar to the earlier embodiment except thumbwheel 65 includes a differently shaped radially outward thumb surface 66 that is more easily engageable by a lock 80. In most respects, vascular intervention device delivery system 60 is similar to the earlier embodiment except turned upside down, and identical numbers are used to identify similar features in both embodiments.

Vascular intervention device delivery system 60 includes a handle 61 within which assembly plate 12 as described earlier is mounted. Assembly plate 12 includes a pivot plate 18 that supports an axle 63 that defines a thumbwheel axis of rotation 64. Like the earlier embodiment, thumbwheel 65 includes both a radially outward thumb surface 66, a spool 67 and a radially outward toothed surface 69. Like the earlier embodiment, thumbwheel 65 may include a spool 67 upon which pull 38 is wound when the device delivery system 60 is operated. In this version, the wire retention/stability sheath 42 terminates at a junction box 43 (not shown in FIG. 7 for sake of clarity) positioned within handle 61. As in the previous version, the pull 38 is positioned within the wire retention/stability sheath 42, and emerges from the junction box 43 to wrap around an idler wheel 44 and return in a reverse direction for being wound onto spool 67 as best shown in FIGS. 7 and 8.

In addition to catch 20 and pivot plate 18, vascular intervention device delivery system 60 includes a lock 80 that allows thumbwheel 65 to be disabled during shipment and during positioning of the distal carrier segment 32 (FIGS. 1-3) at a treatment location within a patient. The lock 80 is moveable between a locked position, as shown, and an unlocked position shown by dashed lines. The lock 80 includes a latch 81 positioned in handle 61 and moveable along a line 82 between the locked position at which the latch 81 engages the radially outward thumb surface 66 of thumbwheel 65, and the unlocked position at which the latch 81 is out of contact with the radially outward thumb surface 66. Lock 80 also includes a pusher 85 that is at least partially positioned outside of handle 61, but on an opposite side of handle 61 from the exposed portion of thumbwheel 65. The pusher may include a wedge 86 that engages a post 83 of latch 81. Post 83 may be oriented perpendicular to the line 82 of action of latch 81. Vascular intervention device delivery system may be enabled by depressing pusher 85 along line 87 to move latch 81 out of contact with radially outward thumb surface 66 of thumbwheel 65.

INDUSTRIAL APPLICABILITY

The present disclosure is generally applicable to vascular intervention device delivery systems, and more particularly to a delivery system for delivery of self expanding stents and other vascular intervention devices with self expanding action. The present disclosure finds specific applicability to delivery of relatively long vascular intervention devices that produce substantial friction on the inner surface of retractable sheath 37, and thus require higher forces on retractable sheath 37 and pull 38 in order to successfully deliver the vascular intervention device to an intended treatment site.

The vascular intervention device delivery system 10, 60 will typically be packaged in a conventional sterile packaging in a known manner for shipment. After a wire guide (not shown) has been positioned in a patient's body across a treatment location, the catheter 30 may be slid over the wire guide to position the distal carrier segment 32 and the attached self expanding stent 45 at the treatment location within the vessel 50 of the patient. Thereafter, the wire guide may be withdrawn or left in place. During this portion of the procedure, the thumbwheel 65 of the vascular intervention device delivery system 60 may be disabled by maintaining the lock 80 in its locked position as shown in FIG. 7. After the distal carrier segment 32 is properly positioned and it is now time to deploy the self expanding stent 45, the user may depress pusher 85 to disengage lock 80 and move latch 81 out of contact with the radially outward thumb surface 66 of thumbwheel 65.

A method of operating vascular intervention device delivery system 10, 60 by first pivoting pivot plate from the locked position to the locked position. Next, the thumbwheel 15, 65 is rotated in a reverse direction to wind pull 38 onto spool 17, 67 to build up tension in the retractable sheath 37 and pull 38 without moving the retractable sheath 37 relative to the distal carrier segment 32 of catheter 30. Next, a portion, which is less than all, of the distal carrier segment 32 is uncovered by continuing to rotate the thumbwheel 15, 65 in the reverse direction. At some point during the delivery procedure, the user may then pause rotation of the thumbwheel 15, 65 in the reverse direction. For instance, the user may pause in order to confirm that the vascular intervention device, such as a self expanding stent 45, is being delivered to the desired location in the vessel 50 of the patient. While the rotation of the thumbwheel is paused, the user may lift their thumb from the thumbwheel 15, 65 and allow the pivot plate 18 to pivot from its unlocked position to its locked position under the action of spring 21. While the rotation of the thumbwheel 15, 65 is paused, tension in the pull 38 and the retractable sheath 37 is maintained by the pivot plate pivoting from the unlocked position to the locked position. This prevents rotation of the thumbwheel 15, 65 in the forward direction. A remaining portion of the distal carrier segment 32 is then uncovered to facilitate complete deployment of the self expanding stent 45 by again pivoting the pivot plate 18 to the unlocked position and resuming rotation of the thumbwheel 15, 65 in the reverse direction until retractable sheath 37 arrives at its second position fully uncovering distal carrier segment 32. Those skilled in the art will appreciate that pivoting of the pivot plate 18 from the locked position to the unlocked position may be accomplished by pushing thumbwheel 15, 65 into the handle 11, 61 against the action of spring 21. Thus, when pressure on thumbwheel 15, 65 is relieved, spring 21 will urge pivot plate 18 back to its locked position to prevent further rotation of thumbwheel 15, 65.

An important aspect of the ratchet operated vascular intervention device delivery system 10, 60 of the present disclosure is to allow for rotation of thumbwheel 15, 65 in one direction only, unless the user permits rotation in the forward direction to intentionally relax tension in pull 38 and retractable sheath 37. This means that the pull 38 and hence the retractable sheath 37 are normally only be pulled proximally. If the thumbwheel 15, 65 were to rotate in both directions, it could cause the pull 38 to slack and possibly jump out of the collection diameter of the spool 17, 67 on thumbwheel 15, 65. Also, by the user keeping the rotation of thumbwheel 15, 65 to one direction only, ratchet 20, 70 allows all of the energy already placed in the system 10, 60 by the user to be maintained. For example, if the user was to partially deploy a self expanding stent 45 that had a deployment force of 30 N they will have to put effort into getting the stent to partially deploy. This effort could have caused the sheath 37 to stretch slightly and also the inner catheter 30 to compress slightly. If this energy were lost when the thumbwheel 15, 65 were released, it would mean that when the deployment was resumed from that point, the user would have to rotate the thumbwheel 15, 65 an amount in order to reestablish tension in the system 10, 60 again before the self expanding stent 45 would continue to deploy. This may be especially important in the case of deploying longer stents that require higher forces.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:
1. A vascular intervention device delivery system comprising:
   a handle that includes a catch positioned therein;
   a pivot plate mounted in the handle, and being pivotable about a first axis with respect to the handle between a locked position and an unlocked position, and the pivot plate supporting an axle that defines a second axis;
   a thumbwheel rotatably mounted on the axle and having a radially outward thumb surface and a radially outward toothed surface;
   wherein the radially outward toothed surface contacts the catch when the pivot plate is pivoted about the first axis with respect to the handle to the locked position to prevent rotation of the thumbwheel in a forward direction, and the radially outward toothed surface moves out of contact with the catch when the pivot plate is pivoted about the first axis with respect to the handle away from the locked position to the unlocked position to permit rotation of the thumbwheel in a reverse direction;
   a catheter with a proximal end attached to the handle, and a distal carrier segment for mounting a vascular intervention device thereon;
   a retractable sheath movable from a first position covering the distal carrier segment, to a second position retracted proximally uncovering the distal carrier segment;
   a pull extending between the thumbwheel and the retractable sheath; and
   the retractable sheath moving responsive to rotation of the thumbwheel in the reverse direction.

2. The vascular intervention device delivery system of claim 1 including a spring operably positioned to bias the pivot plate toward the locked position; and the radially outward toothed surface includes a plurality of teeth in each of four ninety degree rotation angles.

3. The vascular intervention device delivery system of claim 2 wherein the radially outward toothed surface includes at least thirty teeth.

4. The vascular intervention device delivery system of claim 3 wherein the catch is shaped to receive at least one tooth of the radially outward toothed surface when the pivot plate is at the locked position.

5. The vascular intervention device delivery system of claim 4 wherein the first axis is parallel to the second axis; and the first axis is separated for the second axis by a distance that is greater than a diameter of the thumbwheel.

6. The vascular intervention device delivery system of claim 5 wherein both the first axis and the second axis are oriented perpendicular to the pull.

7. The vascular intervention device delivery system of claim 6 wherein the pull includes a metallic band.

8. The vascular intervention device of claim 1 including a self expanding stent positioned radially between the sheath and the distal carrier segment of the catheter.

9. The vascular intervention device delivery system of claim 8 including a spring operably positioned to bias the pivot plate toward the locked position.

10. The vascular intervention device delivery system of claim 9 wherein the catch is shaped to receive at least one tooth of the gear when the pivot plate is at the locked position;

the first axis is parallel to the second axis; and
the first axis is separated for the second axis by a distance that is greater than a diameter of the thumbwheel.

11. The vascular intervention device delivery system of claim 1 including a lock movable between a locked position and an unlocked position;

the lock includes a latch positioned in the handle and moveable along a line between the locked position at which the latch engages the radially outward thumb surface, and the unlocked position at which the latch is out of contact with the radially outward thumb surface; and a pusher at least partially positioned outside the handle and being operably coupled to move the latch from the locked position to the unlocked position.

12. The vascular intervention device delivery system of claim 11 wherein the pusher includes a surface that engages a post that is attached to the latch and oriented perpendicular to the line.

13. The vascular intervention device delivery system of claim 12 including a spring operably positioned to bias the pivot plate toward the locked position.

14. The vascular intervention device delivery system of claim 13 wherein the catch is shaped to receive at least one tooth of the gear when the pivot plate is at the locked position;

the first axis is parallel to the second axis; and
the first axis is separated for the second axis by a distance that is greater than a diameter of the thumbwheel.

15. A method of operating a vascular intervention device delivery system that includes a thumbwheel rotatably mounted in the handle and having a radially outward thumb surface and a radially outward toothed surface; the handle includes a catch positioned therein; a pivot plate mounted in the handle, and being pivotable about a first axis with respect to the handle between a locked position and an unlocked position, and the pivot plate including an axle that defines a second axis; the radially outward toothed surface contacts the catch when the pivot plate is pivoted about the first axis with respect to the handle to the locked position to prevent rotation of the thumbwheel in a forward direction, and the radially outward toothed surface moves out of contact with the catch when the pivot plate is provided about the first axis with respect to the handle away from the locked position to the unlocked position to permit rotation of the thumbwheel in a reverse direction; a catheter with a proximal end attached to the handle, and a distal carrier segment for mounting a vascular intervention device thereon; a retractable sheath movable from a first position covering the distal carrier segment, to a second position retracted proximally uncovering the distal carrier segment; a pull extending between the thumbwheel and the retractable sheath; and the retractable sheath moving responsive to rotation of the thumbwheel in a reverse direction, and the method comprising the steps of:

pivoting the pivot plate from the locked position to the unlocked position;

rotating the thumbwheel in the reverse direction to build up tension in the retractable sheath and pull without moving the retractable sheath relative to the distal carrier segment of the catheter;

uncovering a portion, which is less than all, of the distal carrier segment by continuing to rotate the thumbwheel in the reverse direction;

pausing rotation of the thumbwheel in the reverse direction;

pivoting the pivot plate from the unlocked position to the locked position;

maintaining tension in the pull and the retractable sheath by preventing rotation of the thumbwheel in the forward direction;

pivoting the pivot plate again from the locked position to the unlocked position; and uncovering a remaining portion of the distal carrier segment by resuming rotation of the thumbwheel in the reverse direction.

16. The method of claim 15 wherein the steps of pivoting the pivot plate from the locked position to the unlocked position are performed by pushing the thumbwheel into the handle against the action of a spring.

17. The method of claim 16 wherein the step of pivoting the pivot plate from the unlocked position to the locked position is performed responsive to a force from the spring.

18. The method of claim 15 including a step of enabling operation of the thumbwheel by moving a lock from a locked position to an unlocked position.

19. The method of claim 18 wherein the step of moving a lock includes pushing a pusher to move a latch from engagement with the radially outward thumb surface to being out of contact with the radially outward thumb surface.

* * * * *